(12) United States Patent
Souza et al.

(10) Patent No.: US 9,650,397 B2
(45) Date of Patent: May 16, 2017

(54) 3-((2S,5S)-4-METHYLENE-5-(3-OXOPROPYL)TETRAHYDROFURAN-2-YL)PROPANOL DERIVATIVES, THEIR PREPARATION AND INTERMEDIATES USEFUL THEREOF

(71) Applicant: ALPHORA RESEARCH INC., Mississauga (CA)

(72) Inventors: Fabio E.s. Souza, Mississauga (CA); Jason A. Bexrud, Toronto (CA); Ricardo Orprecio, Etobicoke (CA); Boris Gorin, Oakville (CA)

(73) Assignee: ALPHORA RESEARCH INC., Mississauga, Ontario (CA)

( * ) Notice: Subject to any disclaimer, the term of this patent is extended or adjusted under 35 U.S.C. 154(b) by 0 days.

(21) Appl. No.: 14/890,127

(22) PCT Filed: May 9, 2014

(86) PCT No.: PCT/CA2014/050438
§ 371 (c)(1),
(2) Date: Nov. 9, 2015

(87) PCT Pub. No.: WO2014/183211
PCT Pub. Date: Nov. 20, 2014

(65) Prior Publication Data
US 2016/0090391 A1   Mar. 31, 2016

Related U.S. Application Data

(60) Provisional application No. 61/823,579, filed on May 15, 2013.

(51) Int. Cl.
C07D 307/28 (2006.01)
C07D 493/04 (2006.01)
C07F 7/08 (2006.01)
C07D 493/22 (2006.01)
C07D 307/32 (2006.01)

(52) U.S. Cl.
CPC .......... C07F 7/0812 (2013.01); C07D 307/28 (2013.01); C07D 307/32 (2013.01); C07D 493/22 (2013.01); Y02P 20/55 (2015.11)

(58) Field of Classification Search
CPC ........................ C07D 307/28; C07D 493/04
USPC ........................................ 549/498, 435, 499
See application file for complete search history.

(56) References Cited

U.S. PATENT DOCUMENTS 5,436,238 A  7/1995 Kishi et al.
6,214,865 B1  4/2001 Littlefield

FOREIGN PATENT DOCUMENTS

WO  93/17690  3/1993
WO  99/65894  6/1999
WO  2013/086634  6/2013

OTHER PUBLICATIONS

Jackson, et. al., "A total synthesis of norhalichondrin B," Angewandte Chemi, Wiley-VCH, 2009, 69451 Weinheim, Germany, pp. 1-132.
Narayan, et. al., "Novel second generation analogs of eribulin, Part II: orally available and active against resistant tumors in vivo," Bioorganic & Medicinal Chemistry Letters 21(2011) 1634-1638.
Narayan, et. al., "Novel second generation analogs of eribulin, Part I: compounds containing a lipophilic C32 side chain overcome P-glycoprotein susceptibility," Bioorganic & Medicinal Chemistry Letters 21(2011) 1630-1633.
Narayan, et. al., "Novel second generation analogs of eribulin, Part III: blood-brain barrier permeabillity and in vivo activity in a brain tumor model," Bioorganic & Medicinal Chemistry Letters 21(2011) 1639-1643.
Zheng et. al. "Macrocyclic ketone analogs of halilchondrin B," Bioorganic & Medicinal Chemistry Letters 14 (2004) 5551-5554.
Wang, "Structure-actiity relationships of halichondrin B analogues: modifications at c30-c38," Bioorganic & Medicinal Chemistry Letters 10 (2000) 1029-1032.
Kim, "New synthesis of E7389 c14-c35 and halichondrin c14-c38 building bocks: double-inversion approach," Published on web Oct. 6, 2009, pp. 1-59.
Jackson, "The halichrondins and E7389," Chem. Rev. 2009, 109, pp. 3044-3079.
Choi, "Asymmetric Ni(II)/Cr(ii)-Mediated coupling reaction: catalytis process," Organic letters, 2002, vol. 4, No. 5, pp. 4435-4438.
Kuznetsov, "Induction of morphological and biochemcal apoptosis following prolonged mitotic blockage by halichrondin o macrocycling keton analog E7389," Cancer Res. 2004, pp. 5760-5766, Aug. 16, 2004.

(Continued)

*Primary Examiner* — Charanjit Aulakh
(74) *Attorney, Agent, or Firm* — Jeffrey S. Melcher; Manelli Selter PLLC

(57) ABSTRACT

Discloses is a process for preparation of a compound of formula 11, or a derivative thereof, wherein $PG^1$ is an alcohol protecting group. Also, disclosed are intermediates and processes for their preparation. The compound of formula 11 can be useful in the preparation of halinchondrin analogs.

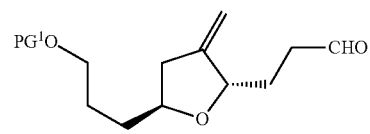

11

9 Claims, No Drawings

(56) References Cited

OTHER PUBLICATIONS

Okouneva, "Ihibition of centromere dynamics by eribulin (e7389) during mitotic metaphase," Mol. DCancer Ther. 2008:7, pp. 2003-2011, published Jul. 21, 2008.
Rudolph, "Early introduction of the amino group to the C27-c35 building block or eribulin," tetrahedon letters 54 (2013), pp. 7059-7061.
Guo, "Toolbox approach to the search for effective ligands for catalytic asymmetric Cr-mediated coupling reactions," published on web Oct. 1, 2009, pp. 1-7.
Trost, "Ru-catalyzed alkene-alkyne coupling. Total synthesis of Amphidinolide P," published on web Nov. 19, 2005, pp. 1-17.
Dong, "New synthesis of E7389 C14-C15 and Halichondrin C14-C38 building blocks: reductive cyclization and ocy-michael cyclizatin approaches," published on web Oct. 6, 2009, pp. 1-5.
Han, "Iridium-catalyzed anti-diastereo- and enantioselective carbonyl (trimethylsilyl)allylation from the alcohol or aldehyde oxidation level," published on web Jun. 11, 2010, pp. 1-4.
Han, "Iridium-catalyzed anti-diastereo- and enantioselective carbonyl (trimethylsilyl)allylation from the alcohol or aldehyde oxidation level," supporting information, published on web Jun. 11, 2010, pp. 1-65.
Jiang, "A practical synthesis of the F-ring of Halichondrin B via ozonolytic desymmetrization of a C2-symmetric dihydroxycyclohexene," JOC note, Aug. 9, 2002, pp. 1-4.
International Search Report and Written Opinion issued in PCT/CA2012/050939, Feb. 15, 2013, pp. 1-10.
Cook, "Total synthesis of (−) Exiguolide," Organic Letters, 2010, vol. 12, No. 4, pp. 744-747.
Jiang, "A novel route to the F-Ring of halichondrin B. Diastereoselection in Pd(O)-mediated meso and C2 diol desymmetrization," Organic Letters 2002, vol. 4, No. 20, pp. 3411-3414.
Choi, "Asymmetric Ni(II)/Cr(II)-mediated coupling reaction: Catalytic Process," Organic Letters 2002, vol. 4, No. 25, pp. 4435-4438.
International Search Report and Written Opinion issued in PCT/CA2012/050859, Jan. 29, 2013, pp. 1-8.
International Preliminary Report on Patentability issued in PCT/CA2012/050897, Jun. 17, 2014, pp. 1-6.
International Preliminary Report on Patentability issued in PCT/CA2012/050939, Jul. 1, 2014, pp. 1-6.
International Preliminary Report on Patentability issued in PCT/CA2013/050254, Jul. 8, 2013, pp. 1-14.
International Preliminary Report on Patentability issued in PCT/CA2014/050438, Jul. 25, 2014, pp. 1-13.
International Preliminary Report on Patentability issued in PCT/CA2014/050504, Jul. 24, 2014, pp. 1-12.
Choi, Synthetic studies on the marine natural product halichondrins, Pure Appl. Chem, vol. 75, No. 1, pp. 1-17, 2003, pp. 1-17.
Sabitha, "Synthesis of the C45-C53 tetrahydropyran domain of norhalichondrins and the C14-C22 tetrahydrofuran domain of the halichondrin family," RSC Advances, 2012, 2, pp. 10157-10159.
Sun, "Synthesis and olefination reactions of an alpha-enal from dacetone glucose," Communications Synthesis, pp. 28-29, Jan. 1982.
Sartillo-Piscil, "Diastereoselective synthesis of 1,2-O-isopropylene-1,6-dioxaspiro[4,4]nonane applying teh methodology of generation of radical cations under non-oxidizing conditions," Tetrahedron Letters 44, (2003), pp. 3919-3921.
Rudolph, "Early introduction of the amino group to the c27-c35 building block of eribulin," Tetrahedron Letters 54 (2013) pp. 7059-7061.
Litaudon, "Isohomohalichondrin B, a New Antitumour Polyether Macrolide from the NEw Zealand Deep-Water Spronge *Lissodendroryx* sp.," Tetrahedron Letters 35, No. 50 (1994) pp. 9435-9438.
Office Action issued in U.S. Appl. No. 14/361,489, Dec. 18, 2014, pp. 1-6.
International Search Report issued in PCT/CA2014/050438, Jul. 25, 2014, pp. 1-3.
Written Opinion issued in PCT/CA2014/050438, Jul. 25, 2014, pp. 1-13.
Jackson, "A total synthesis of norhalichondrin B," Angew. Chem. Int. Ed. vol. 48, No. 13, p. 2346-2350, Mar. 16, 2009.
Jackson, "The halichondrins and E7389," Chem. Rev. vol. 109, p. 3044-3079, Jul. 8, 2009.
Dae-Shick et. al., "New synthesis of E7389 C14-C35 and halichondrin C14-C38 building blocks: double-inversion apprach," J. Am. Chem. Soc. vol. 131, No. 43, p. 1536-15641, Nov. 4, 2009.
Gowravaram, "Synthesis of the C45-053 Tetrahydropyran domain of norhalichondrins and the C14-C22 tetrahydrofuran domain of the halichondrin family," RCS Adv. vol. 27, p. 10157-10159, Nov. 7, 2012.
Tetrahedron Lett. 1994, 35, 9435.
Halichondrin B (Bioorg. Med. Chem. Lett., 2000, 10, 1029 and Bioorg. Med .Chem. Lett., 2004, 14, 5551.
Cancer Res., 2004, 64, 5760.
Mol. Canc. Ther., 2008, 7, 2003.
Kishi (Pure Appl. Chem. 2003, 75, 1-17.
J. Am. Chem. Soc. 2009, 131, 15642-15646.
J. Am. Chem. Soc. 2009, 131, 15636-15641.
Angew. Chem., Int. Ed. 2009, 48, 2346.
Org. Lett. 2002, 4, 3411-3414, J. Org. Chem. 2003, 68, 1150-1153.

3-((2S,5S)-4-METHYLENE-5-(3-OXOPROPYL) TETRAHYDROFURAN-2-YL)PROPANOL DERIVATIVES, THEIR PREPARATION AND INTERMEDIATES USEFUL THEREOF

CROSS-REFERENCE TO RELATED APPLICATION

This application claims the benefit of and priority to U.S. provisional patent application Ser. No. 61/823,579 filed May 15, 2013, under the title 3-((2S,5S)-4-METHYLENE-5-(3-OXOPROPYL)TETRAHYDROFURAN-2-YL)PROPANOL DERIVATIVES, THEIR PREPARATION AND INTERMEDIATES USEFUL THEREOF. The content of the above patent application is hereby expressly incorporated herein by reference into the detailed description hereof.

FIELD

This specification relates to a process for preparation of 3-((2S,5S)-4-methylene-5-(3-oxopropyl)tetrahydrofuran-2-yl)propanol derivatives and intermediates useful thereof.

BACKGROUND

Halichondrins have been disclosed as having anti-cancer and antimitotic activity (*Chem. Rev.* 2009, 109, 3044-3079, incorporated herein by reference). In particular, Halichondrin B has been reported as a potent anticancer agent that was first isolated from the marine sponge *Halichondria okadai* (U.S. Pat. No. 5,436,238; *Tetrahedron Lett.* 1994, 35, 9435 and WO 1993/017690 A1, all incorporated herein by reference). It was further reported that analogs of Halichondrin B bearing only macrocyclic fragment of its molecule (C1-C30 fragment) and having a ketone function instead of ester at C1 position demonstrate anticancer activity similar to Halichondrin B (Bioorg. Med. Chem. Lett., 2000, 10, 1029 and *Bioorg. Med. Chem. Lett.,* 2004, 14, 5551). It was established that such macrocyclic fragment is responsible for induction of mitotic blocks in cancer cells via disruption of tubulin polymerization process that triggers apoptosis of cancerous cells and stops their proliferation (Cancer Res., 2004, 64, 5760 and Mol. Canc. Ther., 2008, 7, 2003). Eribulin mesylate, a macrocyclic C1-keto analog of Halichondrin B, has been reported as having potent anticancer properties (WO 1999/065894 A1, incorporated herein by reference). Eribulin is marketed under the trade name Halaven, and it is also known as E7389, B1939 and ER-086526.

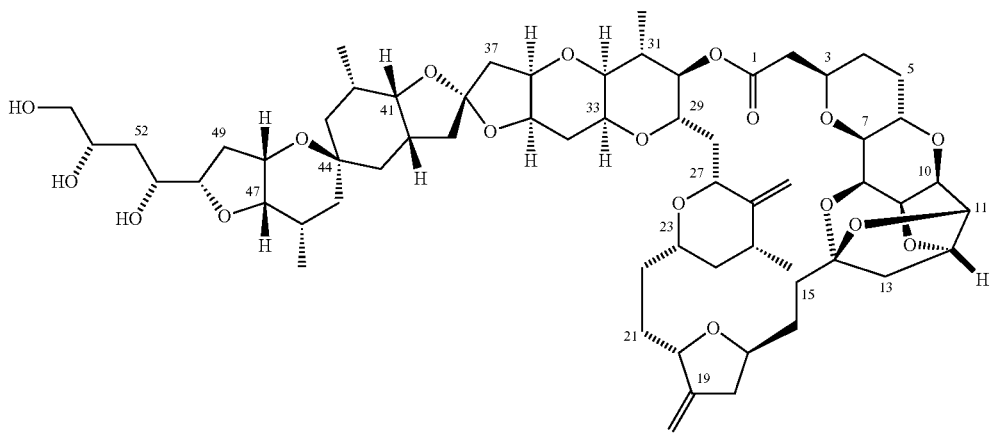

Halichondrin B

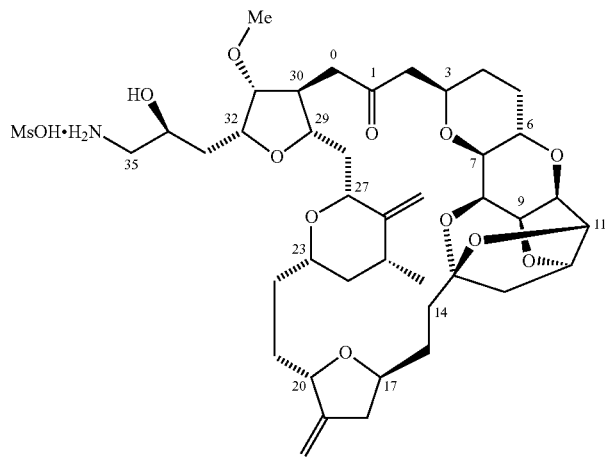

Eribulin mesylate 2,5-disubstituted (2S,5S)-3-methylene-tetrahydrofurans, such as the compound of formula 11a, can be an important building block for the synthesis of the halichondrin natural products and derivatives, as described in U.S. Pat. Nos. 6,214,865 and 5,436,238, and incorporated herein by reference.

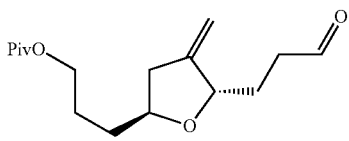

11a wherein Piv is $(CH_3)_3C—C(=O)—$.

The synthesis of compounds, similar to the compound of formula 11a, has been described by Kishi (*Pure Appl. Chem.* 2003, 75, 1-17; *J. Am. Chem. Soc.* 2009, 131, 15642-15646; *J. Am. Chem. Soc.* 2009, 131, 15636-15641), Phillips (*Angew. Chem., Int. Ed.* 2009, 48, 2346) and Burke (*Org. Lett.* 2002, 4, 3411-3414, *J. Org. Chem.* 2003, 68, 1150-1153), all incorporated herein by reference. However, these methods can be undesirable for commercial manufacturing. For example, all these routes rely on asymmetric reactions that, despite their high degree of selectivity, can give rise to epimers, which are of particular concern in cases where the intended use of the molecule is in the manufacture of an active pharmaceutical ingredient. Furthermore, many of these asymmetric reactions employ chiral ligands that are not necessarily easily commercially available, and which can be a hindrance for large scale production.

A number of concerns were addressed in PCT/CA2012/050897 (filed Dec. 14, 2012, and incorporated herein by reference) that provided a route for synthesis of the compound of formula 11a. However, further improvements to improve scalability of the process, such as by improving yields of one or more synthetic steps, improving overall synthetic yield or avoiding or reducing the number of chromatographic purifications, by providing an alternate route to the synthesis of the compound of formula 11a can be desirable.

There is a need in the art for a process for preparation of 3-((2S,5S)-4-methylene-5-(3-oxopropyl)tetrahydrofuran-2-yl)propanol (11a), and its analogs (11), that can be used in the preparation of halichondrin natural products, its derivatives and analogs. In addition, there is a need in the art for a process for preparation of 3-((2S,5S)-4-methylene-5-(3-oxopropyl)tetrahydrofuran-2-yl)prop-1-yl pivaloate (11a), and its analogs (11), that can be prepared from commercially available starting material. Moreover, there is a need in the art for a process for the preparation of 3-((2S,5S)-4-methylene-5-(3-oxopropyl)tetrahydrofuran-2-yl)prop-1-yl pivaloate (11a), and its analogs (11), that can avoid the use of asymmetric reactions, including chiral ligands. In addition, there is a need in the art for a process for preparation of 3-((2S,5S)-4-methylene-5-(3-oxopropyl)tetrahydrofuran-2-yl)prop-1-yl pivaloate (11a), and its analogs (11), where the process is scalable and can lead to a product having high stereochemical purity.

SUMMARY OF THE INVENTION

In one aspect, the specification discloses a process for preparation of a compound of formula 11, or a derivative thereof,

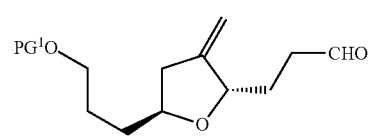

11 the process comprising:
reduction of the compound of formula 8, followed by protection of the resulting alcohol functional group, to form the compound of formula 9, and

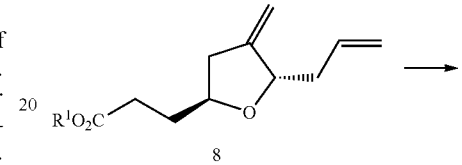

8

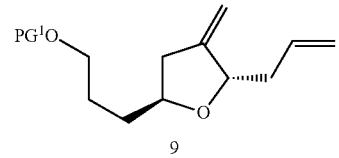

9 oxidation of the compound of formula 9 to form the compound of formula 11

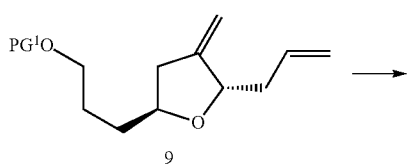

9

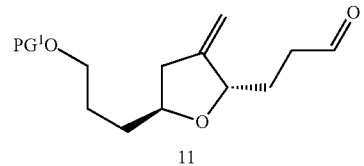

11 wherein $PG^1$ is an alcohol protecting group, and $R^1$ is H or a hydrocarbon.

In another aspect, the specification discloses a compound of formula 8

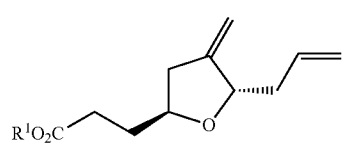

8 wherein $R^1$ is H or a hydrocarbon.

In a further aspect, the specification discloses a compound of formula 7

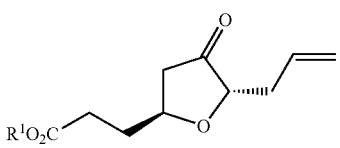

wherein R¹ is H or a hydrocarbon.

In still another aspect, the specification discloses a compound of formula 6,

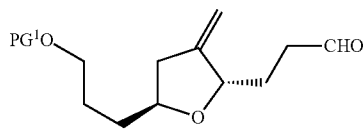

wherein R¹ is H or a hydrocarbon.

In a still further aspect, the specification discloses a process for the preparation of compounds of formula 6, 7 and 8.

DESCRIPTION

As described above, in one aspect, the specification discloses a process for preparation of a compound of formula 11, or a derivative thereof,

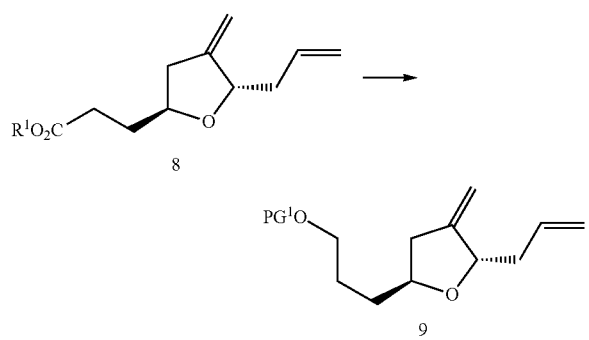

the process comprising:

reduction of the compound of formula 8, followed by protection of the resulting alcohol functional group, to form the compound of formula 9, and

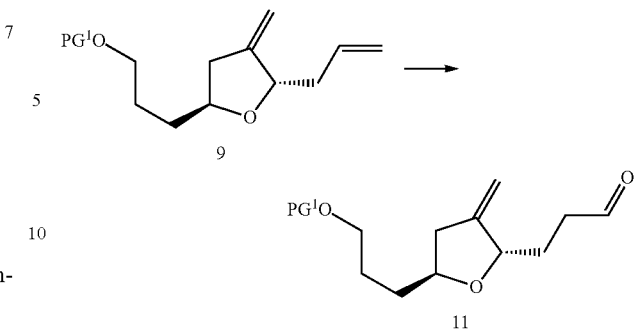

oxidation of the compound of formula 9 to form the compound of formula 11 wherein PG¹ is an alcohol protecting group, and R¹ is H or a hydrocarbon.

The derivatives of the compound of formula 11 relate to the functionalization of the aldehyde functional group and is not particularly limited. The aldehyde functional group can be replaced by other groups, for example and without limitation, an ester, an amide or an acyl halide.

The step of reduction of the compound of formula 8 is not particularly limited and should be known to a skilled worker or can be determined. The reducing agent used should be able to reduce the ester or acid functional group in the compound of formula 8. In one embodiment, for example and without limitation, reduction is performed using a hydride source. The hydride source used is not particularly limited and should be known to a skilled worker or can be determined. In one embodiment, for example and without limitation, the hydride source is lithium aluminum hydride (LAH), lithium triethylborohydride (LiEt$_3$BH), diisobutylaluminum hydride (DIBALH) or sodium bis(2-methoxyethoxy)aluminum hydride (Red-Al) or sodium borohydride (NaBH$_4$).

The reduction of the ester or acid in the compound of formula 8 leads to an alcohol, which is protected to form the compound of formula 9. The alcohol protecting group used is not particularly limited and should be known to a skilled worker or can be determined. In one embodiment, for example and without limitation, the protecting group PG¹ forms an ester, ether or is a silyl-protecting group. In a further, embodiment for example and without limitation, the ester formed is acetyl (Ac), benzoyl (Bz) or pivaloyl (Piv). In another embodiment, for example and without limitation, the ether protecting group formed is benzyl (Bn), β-methoxyethoxymethyl ether (MEM), trityl (Tr), dimethoxy trityl (DMT), methoxymethyl ether (MOM), or the like. In a still further embodiment, for example and without limitation, the silyl protecting group formed is tert-butyldimethylsilyl (TBDMS), tri-iso-propylsilyloxymethyl (TOM), tert-butyldiphenylsilyl (TBDPS), or triisopropylsilyl (TIPS).

The step of oxidation of the compound of formula 9 is not particularly limited and should be known to a skilled worker or can be determined. The oxidation is performed under conditions to selectively oxidize the terminal alkene of the allyl substituent in the compound of formula 9 rather than the exocyclic alkene functional group. In one embodiment, for example and without limitation, the oxidation of the compound of formula 9 is performed using a borane reagent to form the alcohol of formula 10. In a further embodiment, for example and without limitation, the borane oxidation is carried out using disiamylborane (bis-3-methyl-2-butylborane) (Sia$_2$BH), 9-borabycyclo[3,3,1]nonane (9-BBN), dicyclohexylborane (Chx$_2$BH), or dimesitylborane ($C_6H_2Me_3)_2BH$. In a still further embodiment, the borane oxidation is carried out using a peroxide and a base. In a particular embodiment, for example and without limitation, the borane oxidation is carried out using disiamylborane (bis-3-methyl-2-butylborane) ($Sia_2BH$), along with hydrogen peroxide ($H_2O_2$) and sodium hydroxide (NaOH).

A subsequent oxidation step can be carried out to convert the alcohol in the compound of formula 10 to the aldehyde of formula 11. The reagents and conditions used for carrying out the oxidation of the compound of formula 10 to form the compound of formula 11 are not particularly limited and should be known to a skilled worker or can be determined. In one embodiment, for example and without limitation, the step of oxidation of the compound of formula 10 to form the compound of formula 11 is carried out by Collins reagent ($CrO_3.Py_2$), pyridinium dichromate (PDC), Swern oxidation (oxalyl chloride and DMSO), Pfitzner-Moffatt oxidation (carbodiimide and DMSO), Parikh-Doering oxidation (complex $SO_3.Py$ and DMSO), Dess-Martin period inane, Ley oxidation (catalytic tetrapropylammonium perruthenate (TPAP) in the presence of excess N-methylmorpholine N-oxide (NMO)) or Anelli's oxidation (catalytic 2,2,6,6-Tetramethylpiperidin-1-yl)oxyl (TEMPO) in presence of bleach (NaOCl)). In a particular embodiment, for example and without limitation, the oxidation is carried out by Swern oxidation.

The term "hydrocarbon", as used herein, refers to a group that contains hydrogen and carbon, linked generally via a carbon backbone, but may optionally include heteroatoms. Thus, groups like methyl, ethoxyethyl, 2-pyridyl, and trifluoromethyl are considered to be hydrocarbyl for the purposes of this specification. Hydrocarbyl groups include, but are not limited to aryl, heteroaryl, carbocycle, heterocycle, alkyl, alkenyl, alkynyl, and combinations thereof.

The term "heteroatom", is not particularly limited and should be understood by a skilled worker. As used herein, the term means an atom of any element other than carbon or hydrogen. In one embodiment, for the example and without limitation, heteroatoms include nitrogen, oxygen, silicon and sulfur.

The term "alkyl" as used herein is not particularly limited and should be known to a person of skill in the art; and refers to substituted or unsubstituted saturated hydrocarbon groups, including straight-chain alkyl and branched-chain alkyl groups, including haloalkyl groups such as trifluoromethyl and 2,2,2-trifluoroethyl, etc. In one embodiment, for example and without limitation, the alkyl group is a $C_{1-6}$ alkyl.

The term $C_{1-6}$ alkyl in accordance with the specification is not particularly limited and should be known to a person of skill in the art. The $C_{1-6}$ alkyl may be, for example, and without limitation, any straight or branched alkyl, for example, methyl, ethyl, n-propyl, i-propyl, n-butyl, i-butyl, sec-butyl, t-butyl, n-pentyl, i-pentyl, sec-pentyl, t-pentyl, n-hexyl, i-hexyl, 2-methylbutyl, 1,2-dimethylbutyl, 1-ethyl-2-methylpropyl, 2,3-dimethylbutyl, 2,2-dimethylbutyl, 2-ethylbutyl, 2-methylpentyl or 3-methylpentyl.

The term aryl in accordance with the specification is not particularly limited and should be known to a person of skill in the art. The term "aryl" refers to aromatic groups which have at least one ring having a conjugated π-electron system and includes carbocyclic aryl, heterocyclic aryl (also known as heteroaryl groups) and biaryl groups, all of which may be optionally substituted. The aryl groups can include, for example and without limitation, six to fourteen atoms. Examples of aryl group can include, without limitation, phenyl, pyridyl or naphthyl.

The compound of formula 8 used in the synthesis of compound of formula 11 can be prepared by reduction of the compound of formula 7 by converting the ketone functional group into an alkene.

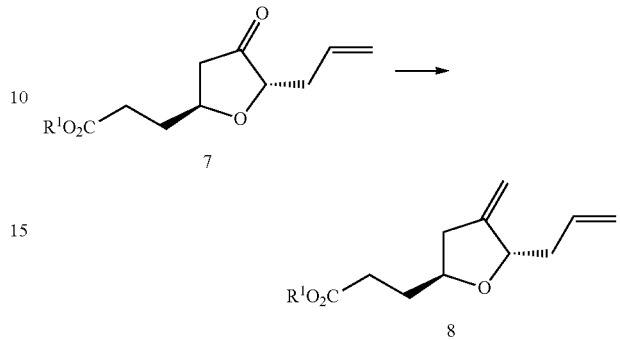

The process for reduction of the ketone functional group in the compound of formula 7 is not particularly limited and should be known to a skilled worker or can be determined. In one embodiment, for example and without limitation, the reagent used for conversion of the ketone to the alkene is methylene triphenylphosphine ($Ph_3P=CH_2$), Tebbe's reagent {$(C_5H_5)_2TiCH_2ClAl(CH_3)_2$}, Petasis reagent {$Cp_2Ti(CH_3)_2$}, or the reaction can be performed via Peterson olefination (using an α-silyl carbanion), or Julia olefination (using an α-arylsulphonyl carbanion), or Kauffmann olefination (by generating the reagent in situ by conversion of different Molybdenum- or Tungsten-halogenides with methyllithium).

In one embodiment in accordance with the specification, the compound of formula 7 is obtained from the compound of formula 6. Oxidation of the compound of formula 6 can be carried out to form the compound of formula 7. The process for oxidizing the alcohol functional group in the compound of formula 6 is not particularly limited, and should be known to a skilled worker, or can be determined. In one embodiment, for example and without limitation, the oxidation of the alcohol functional group in the compound of formula 6 to the ketone in the compound of formula 7 is carried out using a reagent as described above for conversion of the alcohol in the compound of formula 10 to the compound of formula 11.

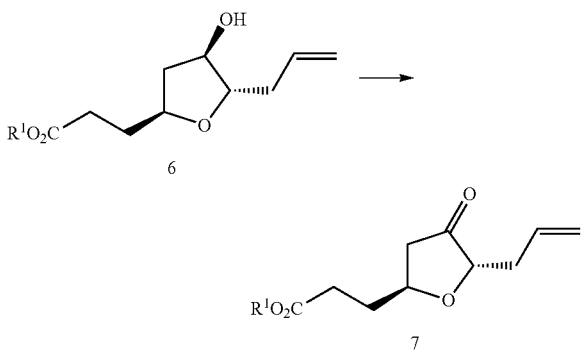

The compound of formula 6, in accordance with the specification, can be formed by coupling of the compound of formula 5 with an allyl-silane of formula 4. The conditions for the coupling reaction of the compound of formula 5 with the allyl-silane of formula 4 are not particularly limited, and in one embodiment, can occur by nucleophilic addition of the allyl-silane of formula 4 to the compound of formula 5.

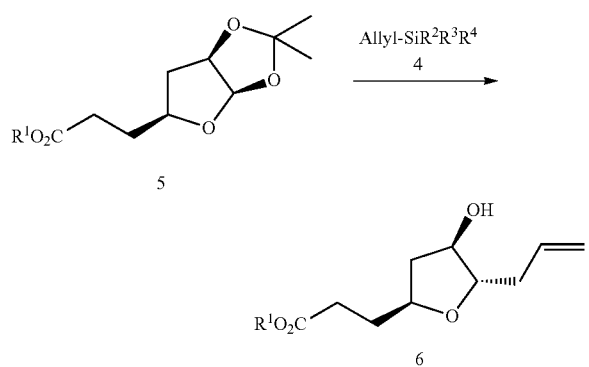

Without being bound to a particular theory, it is believed that the nucleophilic addition of the allyl-silane of formula 4 utilizes the stereochemical features of the compound of formula 5. In particular, the position of the isopropylidene protecting group on the 1,2-diol facilitates nucleophilic addition from the β-face, i.e. from behind the plane of the page, to form the compound of formula 6 having a trans configuration. Hence, the resulting product obtained can have high stereochemical purity (diastereomeric excess).

The conditions for nucleophilic addition reaction of the compound of formula 4 with the compound of formula 5 are not particularly limited, and can be determined. In one embodiment, for example and without limitation, the nucleophilic addition reaction of the compound of formula 4 with the compound of formula 5 is performed in the presence of an activator. The activator used for such a nucleophilic addition reaction is also not particularly limited, and can be determined. In one embodiment, for example and without limitation, the activator is a lewis acid as described in March's Advanced Organic Chemistry: Reactions, Mechanisms, and Structure, 6th Edition, 2007, John Wiley & Sons, Inc. (incorporated herein by reference). Without being bound by a particular theory, in one embodiment, for example and without limitation, the activator can bind with the oxygen atoms on the compound of formula 5, which can increase the electrophilicity of the anomeric carbon centre on the compound of formula 5 and/or can assist in improving the facial selectivity of nucleophilic attack. In one embodiment, for example and without limitation, the activator is a lewis acid, for instance $BF_3$, trimethylsilyl triflate (TMSOTf) or $Ti(O^iPr)Cl_3$.

The allyl-silane of formula 4 used in the nucleophilic addition reaction is not particularly limited, and should be known to a skilled person, or can be determined. In one embodiment, for example and without limitation, in the allyl-silane of formula 4, each $R^2$, $R^3$ and $R^4$ independently is an alkyl, cyclo-alkyl, aryl or hetero-aryl group. In another embodiment, for example and without limitation, each $R^2$, $R^3$ and $R^4$ independently is methyl.

The length of the alkyl or alkanediyl group or the number of atoms in the alkyl group, alkanediyl group or the aryl group are not particularly limited, and should be known to a person of skill in the art or can be determined. In one embodiment, for example and without limitation, the alkyl group is a $C_{1-6}$ alkyl. Similar length of alkanediyl groups can also be used, where appropriate. In another embodiment, for example and without limitation, the aryl group is a $C_{6-14}$ aryl.

In one embodiment in accordance with the description, the compound of formula 5 can be obtained from 1,2:5,6-diisopropylidene glucose (compound of formula 1). The compound of formula 1 is derived from a natural sugar and therefore, can be readily available or can be prepared. Further, the compound of formula 1 can be present as a single stereoisomer. In addition, the reactions performed, as disclosed in the specification, can utilize the stereochemical features of the compound of formula 1 to form a single stereoisomer, resulting in products having high stereochemical purity.

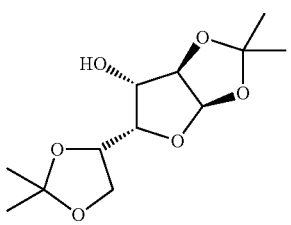

In one embodiment, for example and without limitation, the hydroxyl group of the compound of formula 1 is converted into a leaving group (LG), followed by hydrolysis of the 5,6-isopropylidene protecting group and oxidatively cleaving the diol to form the aldehyde of formula 2.

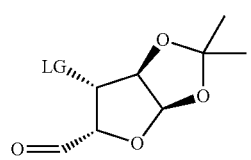

A leaving group as disclosed herein is a molecular fragment or stable species that can be detached from a molecule in a bond-breaking step. The leaving group, in accordance with the specification, is not particularly limited and should be known to a person of skill in the art or can be determined. The ability of a leaving group to depart is correlated with the $pK_a$ of the conjugate acid, with lower $pK_a$ being associated with better leaving group ability. Examples of leaving group include, without limitation, halide or a sulfonate. Halides can include, for example, Cl, Br or I. Examples of sulfonates can include, without limitation, nonaflate, triflate, fluorosulfonate, tosylate, mesylate or besylate. In one embodiment, for example and without limitation, the leaving group is mesylate.

The conditions for hydrolysis of the 5,6-isopropylidene protecting group is not particularly limited, and should be known to skilled worker or can be determined. In one embodiment, for example and without limitation, the 5,6-isopropylidene protecting group is removed using an acid, to yield a diol. The diol can then be oxidatively cleaved to form the aldehyde. The process for oxidative cleavage of the diol is not particularly limited, and should also be known to a skilled worker or can be determined. In one embodiment, for example and without limitation, the oxidative cleavage is performed using periodate oxidation. In a further embodiment, for example and without limitation, the periodate used is NaIO$_4$. The process for conversion of the compound of formula 1 into the compound of formula 2 can also be performed as described in *Synthesis*, 1982, 28-29, incorporated herein by reference.

The compound of formula 2 can undergo an elimination reaction in the presence of a base to remove the leaving group and form an alkene, and the aldehyde functionality can undergo a Wittig or a Horner-Wadsworth Emmons reaction, by reacting with a Ph$_3$P=CHCO$_2$Me (9), or analog thereof, to form the compound of formula 3. The base used for the elimination reaction is not particularly limited, and should be known to skilled worker or can be determined. In one embodiment, for example and without limitation, the base is 1,5-diazabicyclo[4.3.0]non-5-ene (DBN). The analog of the compound of formula 9 is not particularly limited. In one embodiment, for example and without limitation, the phosphonate reagent (EtO)$_2$P(=O)—CH$_2$CO$_2$Me is used. In another embodiment, for example and without limitation, the methyl group in the ester functionality has been replaced by an alternate alkyl group, such as, for example and without limitation, ethyl, propyl or butyl.

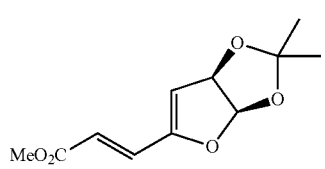

3

The compound of formula 3 can then undergo hydrogenation of the alkene, to form the compound of formula 5.

The conditions for the hydrogenation reaction are not particularly limited and should be known to a skilled worker or can be determined. In one embodiment, for example and without limitation, the hydrogenation reaction is performed using a hydrogenation catalyst, such as for example and without limitation, palladium on carbon (Pd/C). Again in the hydrogenation reaction, and without being bound to a particular theory, it is believed that the presence of the 1,2-isopropylidene group can direct hydrogenation from the β-face, i.e. below the plane of the paper, which can lead to a stereoisomer having the desired stereochemistry, in high diastereomeric excess (d.e.).

As noted above, using the process disclosed in the specification, compounds having high diastereomeric purity can be obtained. In one embodiment, for example and without limitation, the chiral purity of any one of the compounds of formula 2 to 11 is about 99.0%, 99.1%, 99.2%, 99.3% 99.4%, 99.5%, 99.6%, 99.7%, 99.8%, 99.9% d.e. or any values in between.

In one embodiment, for example and without limitation, the synthesis of the compound of formula 11 can be carried out from the compound of formula 1, as shown in Scheme 1 below.

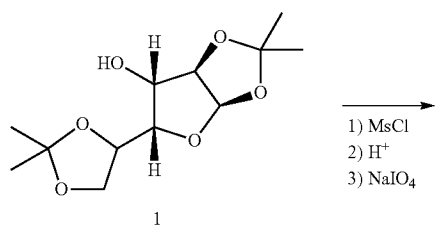

1

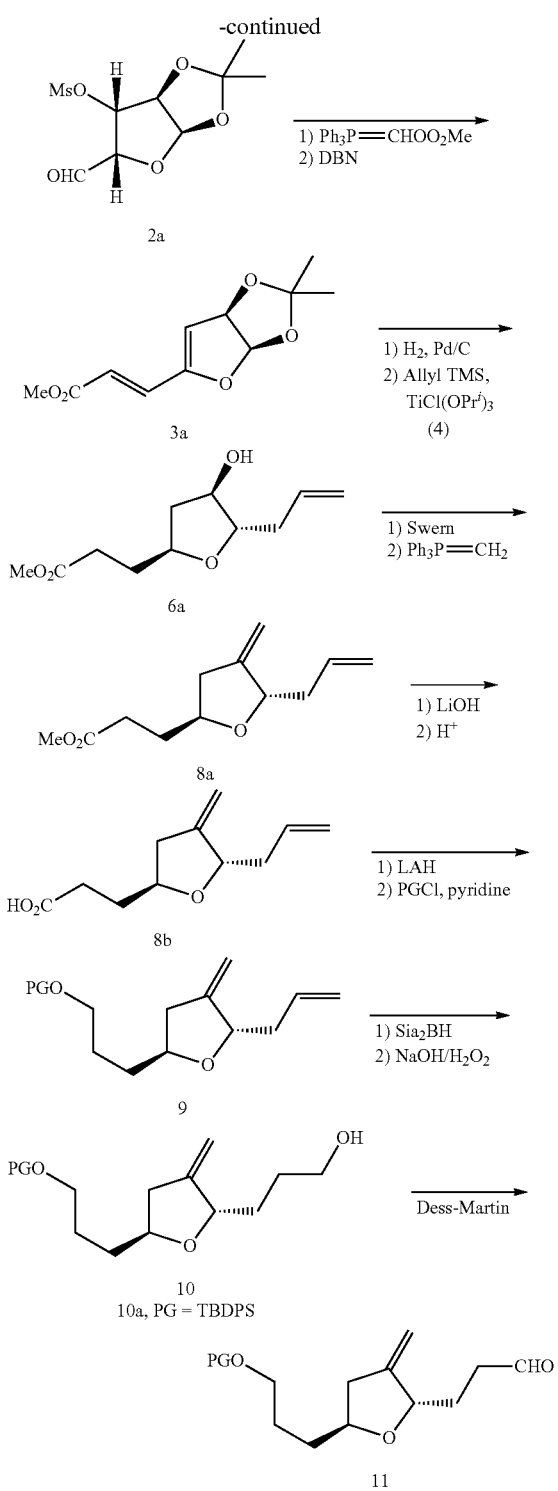

In brief, the hydroxyl group of the 1,2:5,6-diisopropylidene glucose (1) can be converted into a leaving group, followed by removal of the 5,6-isopropylidene protecting group and oxidative cleavage of the resulting diol to form the compound of formula 2a. Reaction with Ph$_3$P=CHCO$_2$Me and elimination reaction using a base results in formation of compound 3a. Hydrogenation of compound 3a and coupling of the resulting alkane with an allyl-silane of formula 4 leads to the compound of formula 6a. Swern oxidation of the alcohol in the compound of formula 6a can be carried out to form the ketone, which can then be olefinated to give the exocylic alkene of formula 8a. The compound of formula 8a can undergo hydrolysis to form the acid (8b). Reduction, using lithium aluminum hydride, followed by protection of the resulting alcohol is carried out to form the compound of formula 9. Selective oxidation of the alkene on the allyl substituent in the compound of formula 9 using disiamylborane, sodium hydroxide and hydrogen peroxide leads to the alcohol of formula 10. Further oxidation of the alcohol to the aldehyde is performed to form the compound of formula 11.

EXAMPLES

The following examples are illustrative and non-limiting, and represent specific embodiments of the present invention.

The compound of formula 2a can be prepared as described in *Synthesis* 1982, 28-29, incorporated herein by reference.

Disiamyl borane was prepared as a solution in tetrahydrofuran according to the procedures described in *Org. Lett.* 2012, 14, 2262-2265, incorporate herein by reference.

Example 1

Preparation of Compound of Formula 3a

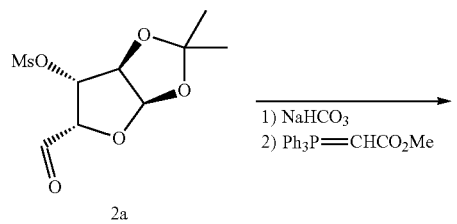

Compound 2a (1 wt) was dissolved in a mixture of methanol (4.6 v) and water (1.8 v). NaHCO$_3$ (0.6 wt) was added and the mixture heated to reflux until reaction was complete as determined by thin layer chromatography (TLC). The mixture was cooled to ambient temperature and methyl triphenylphosphoranylidene acetate (1.14 wt) was added. After stirring for 0.5 hr, the reaction mixture was quenched with water and extracted 2 times with methyl t-butyl ether (MTBE). The combined organic extract was dried over Na$_2$SO$_4$, filtered and concentrated under reduced pressure to give a residue. The residue was triturated with methyl t-butyl ether (3.6 v), filtered and rinsed with methyl t-butyl ether. The filtrate was concentrated to give compound 3a (1.2 wt) as a mixture of cis/trans-isomers.

Example 2

Preparation of Compound of Formula 3a

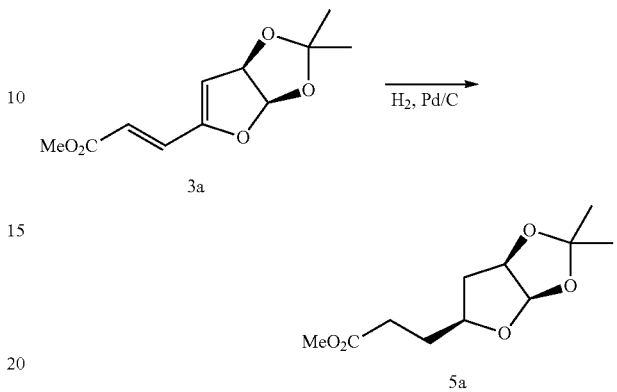

A solution of compound 3a (1 wt), dissolved in isopropanol (iPrOH) (20 v) was added to 10 wt % palladium on carbon (Pd(C)) (0.4 wt) in a Parr hydrogenation flask. The reaction vessel was pressurized to 40 psi with H$_2$ (gas) and maintained at this pressure, while being agitated for 20 hours. Following this, the reaction mixture was filtered through a plug of celite, which was then rinsed with MeOH (25 v). The combined filtrate and MeOH rinse was concentrated under reduced pressure to yield a viscous oil, which was subjected to column chromatography (SiO$_2$, 1:1 Heptanes:EtOAc) to yield compound 5a (0.4 eq) as a colorless oil.

Example 3

Preparation of Compound of Formula 6a

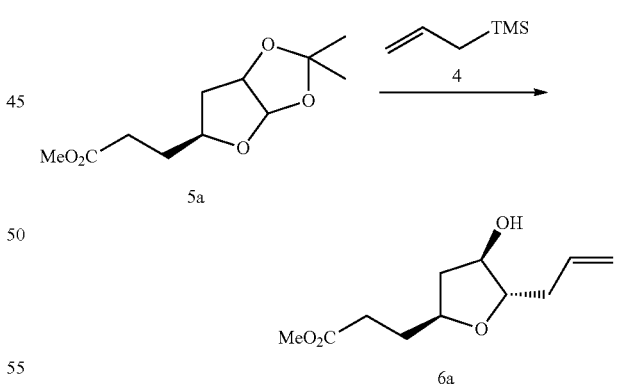

To a nitrogen purged, 3-necked round bottomed flask equipped with a thermometer, and stir bar, was added a solution of compound 5a (1 eq) and allyltrimethylsilane 4 (1.5 eq) dissolved in anhydrous CH$_2$Cl$_2$ (10 v). The solution was cooled to 0-5° C. and then a solution of Ti(O$^i$Pr)Cl$_3$ (1.2 eq) dissolved in anhydrous CH$_2$Cl$_2$ (10 v) was added at a sufficiently slow rate such that the internal temperature did not exceed 5° C. The reaction was then quenched by the slow addition of 1N HCl (aq) (10 v). The layers were separated, and the aqueous phase was further extracted with CH$_2$Cl$_2$ (3×10 v). The combined organic extracts were then washed successively with saturated NaHCO$_3$ (aq), followed by brine and then dried over Na$_2$SO$_4$. Removal of the drying agent by filtration, followed by concentration under reduced pressure afforded a crude residue which was then passed through a silica plug, eluting with MTBE. 6a (0.83 eq, including 10% of the all-syn diastereomer) was obtained as a yellow oil upon removal of the solvents under reduced pressure, and used directly for the next step without any further purification.

Example 4

Preparation of Compound of Formula 7a

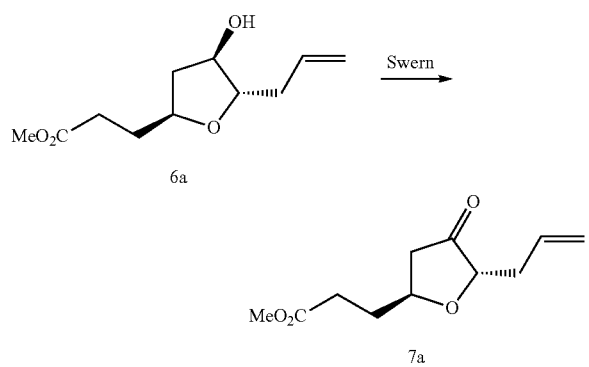

A solution of (COCl)$_2$ (1.5 eq) dissolved in anhydrous CH$_2$Cl$_2$ (10 v), stirring under nitrogen in a round bottomed flask, was cooled to below −70° C. using a dry ice/acetone bath. Dimethylsulfoxide (DMSO) (2 eq) was then slowly added and the mixture was stirred for 10 minutes. To the resulting solution of dimethylchlorosulfonium chloride was added 6a (1 eq) over 20 minutes while the temperature of the solution was maintained below −70° C. After stirring for 30 minutes, triethylamine (NEt$_3$) (5 eq) was slowly added and the reaction was left to stir for an additional 120 minutes below −70° C., before being allowed to warm to ambient temperature. The reaction was quenched with water (10 v), the layers were separated and the aqueous phase was further extracted with CH$_2$Cl$_2$ (10 v). The combined organic extracts were washed with brine, dried over Na$_2$SO$_4$, filtered, and concentrated under reduced pressure. The resulting crude residue was passed through a silica plug eluting with a mixture of EtOAc/heptane (1:1), and then concentrated under reduced pressure to afford 7a (0.93 eq) as a yellow oil. The product was used directly for the next step without any further purification.

Example 5

Preparation of Compound of Formula 8a

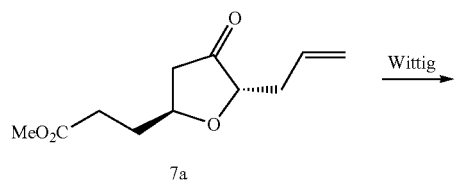

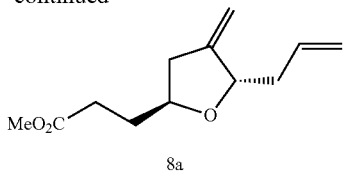

To a nitrogen purged round bottomed flask equipped with a stir bar was added methyltriphenylphosphonium bromide (1.5 eq), and potassium tert-butoxide (KOtBu) (1.5 eq). The flask was cooled using an ice/water bath, and then anhydrous tetrahydrofuran (THF) (20 v) was slowly added. After stirring the resulting bright yellow slurry for 1 hour, 7a (1 eq) was added over a span of 20 minutes. The reaction was left to stir for a further 30 minutes before being quenched with water (10 v). The layers were separated and the aqueous phase was extracted with ethyl acetate (EtOAc) (3×10 v). The combined organic extracts were washed with brine, dried over Na$_2$SO$_4$, filtered, and concentrated under reduced pressure. The resulting crude residue was triturated with heptanes and the solids were removed by vacuum filtration. Concentration of the filtrate under reduced pressure afforded 8a (0.91 eq) as a yellow oil. This product was used directly for the next step without any further purification.

Example 6

Preparation of Compound of Formula 9a

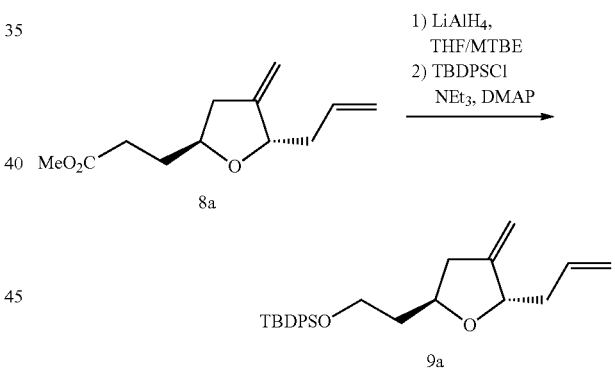

8a (1 eq), dissolved in MTBE/THF (4:1, 1 v), was slowly added to a nitrogen filled round bottomed flask containing a magnetically stirred slurry of LiAlH$_4$ (2 eq) in MTBE/THF (4:1, 6 v) at 0-5° C. The reaction mixture was stirred for 20 minutes before being allowed to warm to ambient temperature over 40 minutes. After the reaction was judged to be complete by thin layer chromatography (TLC), the slurry was again cooled to 0-5° C. and the remaining lithium aluminum hydride reagent was quenched by the successive, slow addition of water (0.4 v), 1N NaOH (0.4 v) followed by more water (1.2 v). The mixture was stirred for 20 minutes, Na$_2$SO$_4$ was added and, after stirring for a further 20 minutes, all of the solids were removed by vacuum filtration. Concentration of the filtrate afforded the crude product (1.0 eq) as a colorless oil. This crude product was dissolved in toluene (12 v) and again concentrated to dryness before being set stirring as a solution in anhydrous CH$_2$Cl$_2$ (45 v) under nitrogen atmosphere. The solution was cooled to 0-5° C. with an ice/water bath. Triethylamine (NEt$_3$) (5 eq), dimethylaminopyridine (DMAP) (0.1 eq) and t-butyldiphenylsilylchloride (TBDPSCl) (1.2 eq) were then all added in succession. The cooling bath was removed and the reaction was left to stir for 20 hours. Following this the reaction was treated with water (10 v) and then transferred to a separatory funnel with CH$_2$Cl$_2$ (10 v). The layers were separated, and the organic phase was further washed with brine, dried over Na$_2$SO$_4$, filtered and concentrated to dryness under reduced pressure. The resulting crude residue was purified by chromatography (SiO$_2$, Heptane/EtOAc) to afford 9a (0.71 eq) as a light yellow oil.

Example 7

Preparation of Compound of Formula 8b

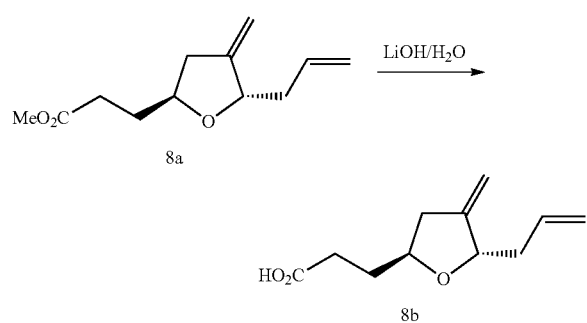

To a round bottomed flask equipped with a stir bar was added a solution of 8a (1 eq) dissolved in MeOH/water (14 v, 2:1). The solution was cooled using an ice/water bath. LiOH.H$_2$O (5 eq) was then added in a few portions, and the mixture was stirred for 1.5 hours. Following this the reaction solution was diluted with 1N HCl (aq) (40 v), and extracted with EtOAc (3×80 v). The combined organic extracts were washed with brine, dried over Na$_2$SO$_4$, filtered, and concentrated in vacuo to afford 8b (1 eq) as a light yellow oil, which may crystallize upon standing.

Example 8

Preparation of Compound of Formula 11a

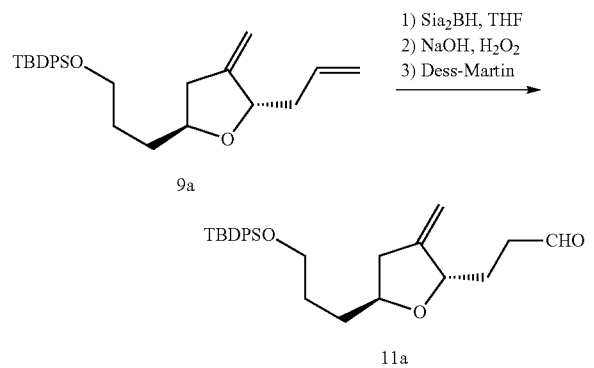

To a round bottomed flask equipped with a stir bar was added a solution of 9a (1 eq) in THF (20 v). The solution was cooled to −30° C. and disiamylborane solution (0.5M in THF, 2 eq) was then added dropwise, so as to keep the temperature below −20° C. A second (2 eq) and third (1 eq) portions of disiamylborane solution were added at 30 min. intervals, after which an aqueous solution of NaOH (3M, 10 v) was added to the reaction mixture. Aqueous H$_2$O$_2$ (30% w/w, 10 v) was added dropwise, keeping the reaction temperature below 20° C., after which the reaction mixture was agitated at room temperature overnight. The phases were separated and the organic layer was washed with brine (21 v) and concentrated to dryness. The residue was purified by chromatography (SiO$_2$, Heptane/dichloromethane, then dichloromethane/EtOAc) to afford alcohol 10a (1 eq) as a yellow oil.

Alcohol 10a (1 eq) was dissolved in dichloromethane (40 v) and treated sequentially with solid NaHCO$_3$ (0.4 parts w/w) and Dess-Martin periodinane (2.2 eq). After agitating for 2 h, the reaction mixture was cooled to 5° C. and quenched with a mixture of aqueous solutions of NaHCO$_3$ (saturated, 20 v) and Na$_2$SO$_3$ (10% w/w, 20 v). The phases were separated and the aqueous layer was back extracted with dichloromethane (8 v). The combined organic layers were washed with brine (32 v) and concentrated to dryness. The residue was purified by chromatography (SiO$_2$, toluene/MTBE) to afford aldehyde 11a (0.89 eq) as a yellow oil.

Embodiments

1. A process for preparation of a compound of formula 11, or a derivative thereof,

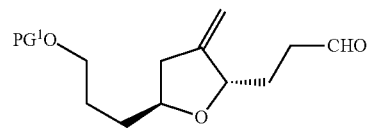

the process comprising:

reduction of the compound of formula 8, followed by protection of the resulting alcohol functional group, to form the compound of formula 9, and

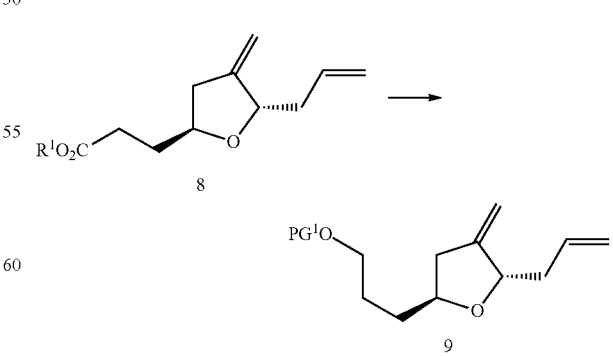

oxidation of the compound of formula 9 to form the compound of formula 11

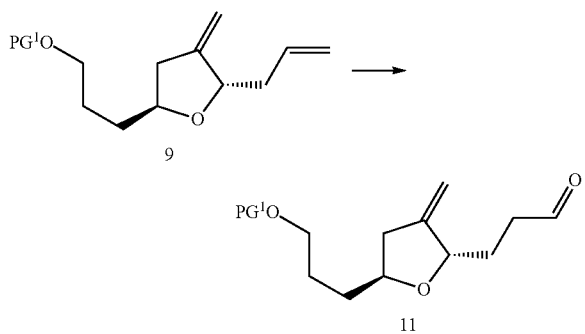

wherein PG¹ is an alcohol protecting group, and R¹ is H or a hydrocarbon.

2. The process according to embodiment 1, wherein the step of oxidation of the compound of formula 9 is performed by hydroboration-oxidation to form the compound of formula 10,

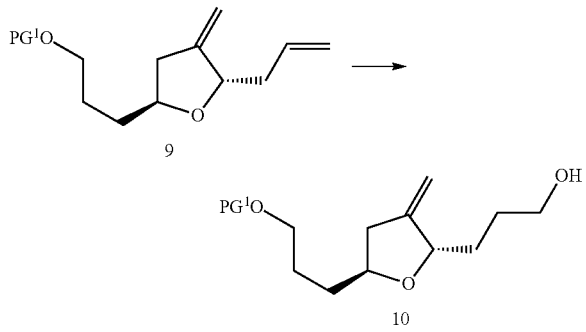

followed by oxidation of the compound of formula 10 to form the compound of formula 11

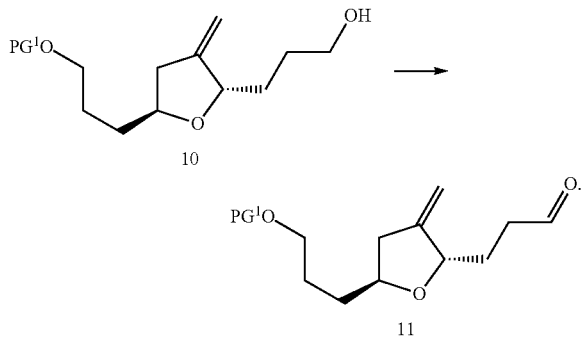

3. The process according to embodiment 2, wherein the hydroboration oxidation is carried out using disiamylborane (bis-3-methyl-2-butylborane) (Sia$_2$BH), 9-borabycyclo[3,3,1]nonane (9-BBN), dicyclohexylborane (Chx$_2$BH), or dimesitylborane (C$_6$H$_2$Me$_3$)$_2$BH, along with a peroxide.

4. The process according to embodiment 2, wherein the hydroboration oxidation is carried out using disiamylborane (Sia$_2$BH), sodium hydroxide (NaOH) and hydrogen peroxide (H$_2$O$_2$).

5. The process according to any one of embodiments 2 to 4, wherein the step of oxidation of the compound of formula 10 to form the compound of formula 11 is carried out by Collins reagent (CrO$_3$.Py$_2$), pyridinium dichromate (PDC), Swern oxidation (oxalyl chloride and DMSO), Pfitzner-Moffatt oxidation (carbodiimide and DMSO), Parikh-Doering oxidation (complex SO$_3$.Py and DMSO), Dess-Martin periodinane, Ley oxidation (catalytic tetrapropylammonium perruthenate (TPAP) in the presence of excess N-methylmorpholine N-oxide (NMO)) or Anelli's oxidation (catalytic 2,2,6,6-Tetramethylpiperidin-1-yl)oxyl (TEMPO) in presence of bleach (NaOCl)).

6. The process according to any one of embodiments 1 to 5, wherein R¹ is a hydrocarbon, and the step of reducing the compound of formula 8 to form the compound of formula 9 is carried out by first hydrolyzing the compound of formula 8 where R¹ is a hydrocarbon to form a compound of formula 8 where Fe is H, followed by reduction of the compound of formula 8 to form the compound of formula 9.

7. The process according to any one of embodiments 1 to 6, wherein the step of reducing the compound of formula 8 to form the compound of formula 9 is carried out using lithium aluminum hydride (LAH), diisobutyl aluminum hydride (DIBALH), sodium borohydride (NaBH$_4$) or lithium triethylborohydride (LiEt$_3$BH).

8. The process according to any one of embodiments 1 to 7, wherein PG¹ is acetyl (Ac), benzoyl (Bz), pivaloyl (Piv), benzyl (Bn), β-methoxyethoxymethyl ether (MEM), trityl (Tr), dimethoxy trityl (DMT), methoxymethyl ether (MOM), tert-butyldimethylsilyl (TBDMS), tert-butyldiphenylsilyl (TBDPS), tri-iso-propylsilyloxymethyl (TOM), or triisopropylsilyl (TIPS).

9. The process according to any one of embodiments 1 to 8, wherein when R¹ is a hydrocarbon, the hydrocarbon is an alkane or aryl, having one or more heteroatoms.

10. The process according to any one of embodiments 1 to 9, wherein the compound of formula 8 is formed by conversion of the ketone functional group in the compound of formula 7 to an alkene functional group, to form the compound of formula 8

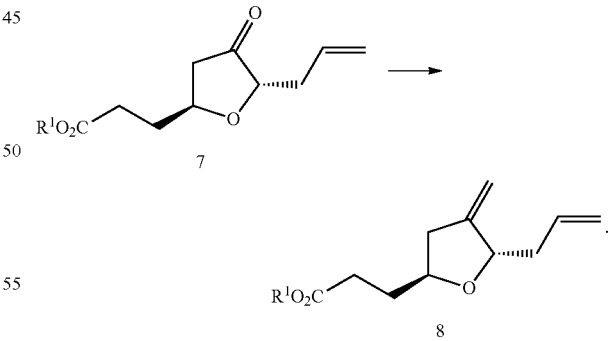

11. The process according to embodiment 10, wherein the step of conversion of the ketone to an alkene is carried out using Ph$_3$P═CH$_2$, Tebbe's reagent, Petasis reagent, Peterson olefination, Julia olefination, or Kauffman olefination.

12. The process according to embodiment 10 or 11, wherein the compound of formula 7 is formed by oxidation of the compound of formula 6 to convert the hydroxyl functional group into a ketone functional group

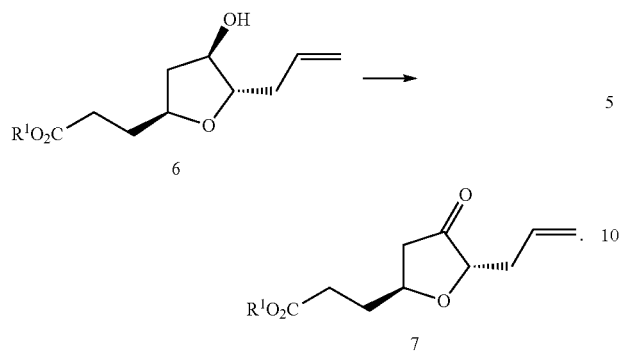

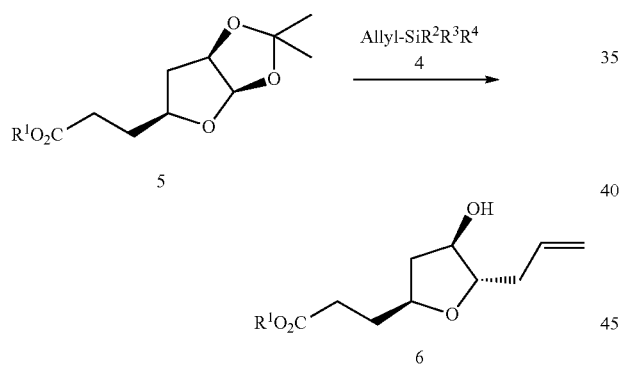

wherein R², R³ and R⁴ each independently is an alkyl, cyclo-alkyl, aryl or hetero-aryl group.

15. The process according to embodiment 14, wherein R², R³ and R⁴ each independently is a $C_{1-6}$ alkyl, $C_{6-14}$ aryl or $C_{5-14}$ hetero-aryl group.

16. The process according to embodiment 14, wherein R², R³ and R⁴ each independently is methyl.

17. The process according to any one of embodiments 14 to 16, wherein the coupling reaction is performed in the presence of an activator.

18. The process according to embodiment 17, wherein the activator is $Ti(O^iPr)Cl_3$.

19. The process according to embodiment 17, wherein the activator is boron trifluoride.

20. The process according to any one of embodiments 14 to 19, wherein the compound of formula 5 is formed from the compound of formula 1

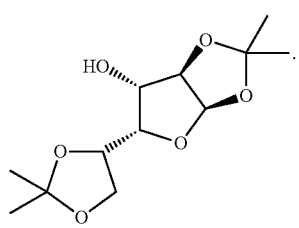

21. The process according to embodiment 20, wherein the compound of formula 5 is obtained by:
converting the hydroxyl group of compound of formula 1 into a leaving group, hydrolyzing the 5,6-isopropylidene protecting group and oxidatively cleaving the diol to form the aldehyde of formula 2;

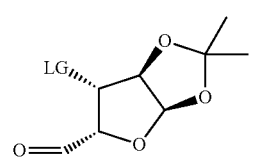

reacting the compound of formula 2 with $Ph_3P=CHCO_2Me$, or an analog thereof, followed by reacting the resulting acrylate with a base to eliminate the leaving group to form the compound of formula 3;

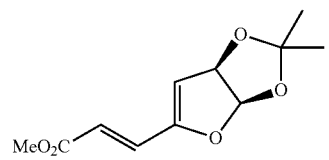

hydrogenating the alkene to reduce the double bonds to form an embodiment of the compound of formula 5, where R¹ is methyl.

22. The process according to embodiment 21, wherein the leaving group formed is a sulfonate based leaving group.

23. The process according to embodiment 21, wherein the leaving group formed is a mesylate.

24. The process according to any one of embodiments 21 to 23, wherein hydrolysis of the 5,6-isopropylidene protecting group of the compound of formula 1 is performed using an acid.

25. The process according to any one of embodiments 21 to 24, wherein the oxidative cleavage of the diol obtained from the compound of formula 1 is performed by periodate oxidation.

26. The process according to any one of embodiments 21 to 24, wherein the oxidative cleavage of the diol obtained from the compound of formula 1 is performed by sodium periodate.

27. The process according to any one of embodiments 21 to 26, wherein the base for the elimination reaction is 1,5-Diazabicyclo(4.3.0)non-5-ene (DBN).

28. The process according to any one of embodiments 21 to 27, wherein the hydrogenation of the compound of formula 3 is performed using $H_2$ and Pd/C.

13. The process according to embodiment 12, wherein the step of oxidation of the compound of formula 6 is carried out by Swern oxidation (oxalyl chloride and DMSO), Pfitzner-Moffatt oxidation (carbodiimide and DMSO), Parikh-Doering oxidation (complex $SO_3.Py$ and DMSO), Dess-Martin periodinane, Ley oxidation (catalytic tetrapropylammonium perruthenate (TPAP) in the presence of excess N-methyl-morpholine N-oxide (NMO)) or Anelli's oxidation (catalytic 2,2,6,6-Tetramethylpiperidin-1-yl)oxyl (TEMPO) in presence of bleach (NaOCl)).

14. The process according to embodiment 12 or 13, wherein the compound of formula 6 is formed by coupling the compound of formula 5 with the allyl-silane of formula 4 to form the compound of formula 6

29. The compound of formula 8

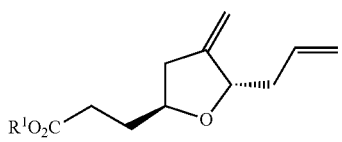

wherein $R^1$ is H or a hydrocarbon.

30. The compound of formula 7

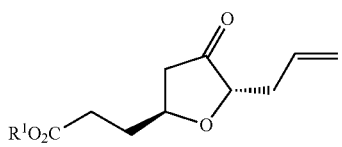

wherein $R^1$ is H or a hydrocarbon.

31. The compound of formula 6

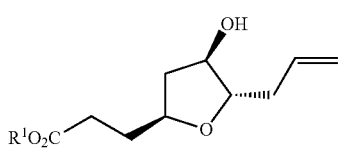

wherein $R^1$ is H or a hydrocarbon.

32. A process for preparation of the compound of formula 6

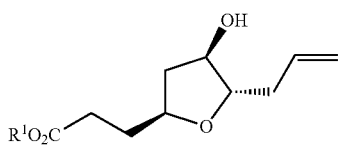

wherein $R^1$ is H or a hydrocarbon, the process comprising:
coupling the compound of formula 5 with the allyl-silane of formula 4 to form the compound of formula 6

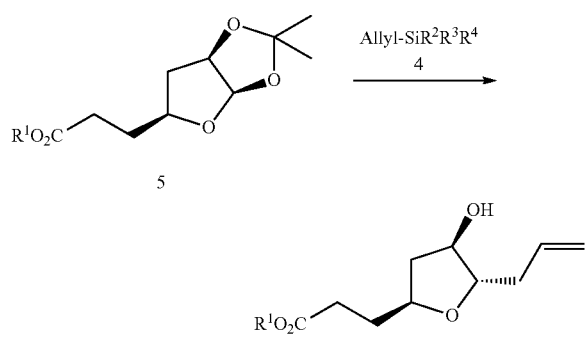

wherein $R^2$, $R^3$ and $R^4$ each independently is an alkyl, cyclo-alkyl, aryl or hetero-aryl group.

33. The process according to embodiment 32, wherein $R^2$, $R^3$ and $R^4$ each independently is a $C_{1-6}$ alkyl, $C_{6-14}$ aryl or $C_{5-14}$ hetero-aryl group.

34. The process according to embodiment 32, wherein $R^2$, $R^3$ and $R^4$ each independently is methyl.

35. The process according to any one of embodiments 32 to 34, wherein the coupling reaction is performed in the presence of an activator.

36. The process according to embodiment 35, wherein the activator is $Ti(O^iPr)Cl_3$.

37. The process according to embodiment 35, wherein the activator is boron trifluoride.

38. The process according to any one of embodiments 32 to 37, wherein the compound of formula 5 is formed from the compound of formula 1

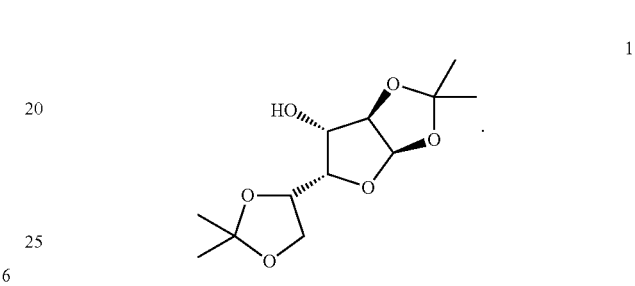

39. The process according to embodiment 38, wherein the compound of formula 5 is obtained by:
converting the hydroxyl group of compound of formula 1 into a leaving group, hydrolyzing the 5,6-isopropylidene protecting group and oxidatively cleaving the diol to form the aldehyde of formula 2;

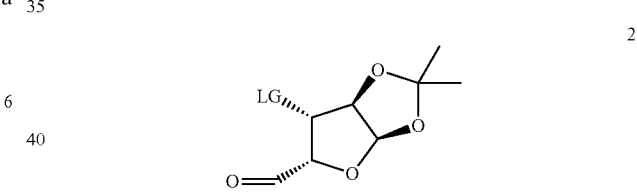

reacting the compound of formula 2 with $Ph_3P=CHCO_2Me$, or an analog thereof, followed by reacting the resulting acrylate with a base to eliminate the leaving group to form the compound of formula 3;

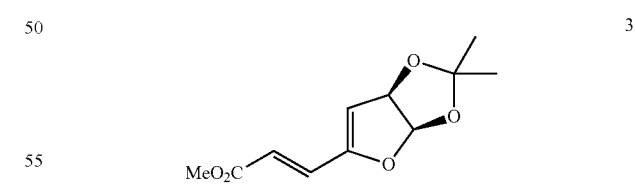

hydrogenating the alkene to reduce the double bonds to form the compound of formula 5.

40. The process according to embodiment 39, wherein the leaving group formed is a sulfonate based leaving group.

41. The process according to embodiment 39, wherein the leaving group formed is a mesylate.

42. The process according to any one of embodiments 39 to 41, wherein hydrolysis of the 5,6-isopropylidene protecting group of the compound of formula 1 is performed using an acid.

43. The process according to any one of embodiments 39 to 42, wherein the oxidative cleavage of the diol obtained from the compound of formula 1 is performed by periodate oxidation.

44. The process according to any one of embodiments 39 to 42, wherein the oxidative cleavage of the diol obtained from the compound of formula 1 is performed by sodium periodate.

45. The process according to any one of embodiments 39 to 44, wherein the base for the elimination reaction is 1,5-Diazabicyclo(4.3.0)non-5-ene (DBN).

46. The process according to any one of embodiments 39 to 45, wherein the hydrogenation of the compound of formula 3 is performed using $H_2$ and Pd/C.

47. A process for the preparation of the compound of formula 7

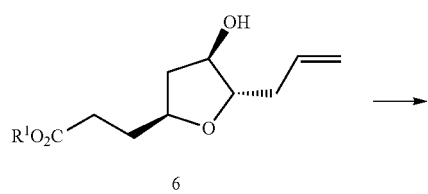

wherein $R^1$ is H or a hydrocarbon, the process comprising:
oxidizing the compound of formula 6 to convert the hydroxyl functional group into a ketone functional group

48. The process according to embodiment 47, wherein the step of oxidation of the compound of formula 6 is carried out by Swern oxidation (oxalyl chloride and DMSO), Pfitzner-Moffatt oxidation (carbodiimide and DMSO), Parikh-Doering oxidation (complex $SO_3.Py$ and DMSO), Dess-Martin periodinane, Ley oxidation (catalytic tetrapropylammonium perruthenate (TPAP) in the presence of excess N-methylmorpholine N-oxide (NMO)) or Anelli's oxidation (catalytic 2,2,6,6-Tetramethylpiperidin-1-yl)oxyl (TEMPO) in presence of bleach (NaOCl)).

49. The process according to embodiment 47 or 48, wherein the compound of formula 6 is formed by the process as defined in any one of embodiments 32 to 46.

50. A process for preparation of the compound of formula 8

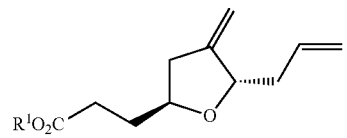

wherein Fe is H or a hydrocarbon, the process comprising:
converting the ketone functional group in the compound of formula 7 to an alkene functional group, to form the compound of formula 8

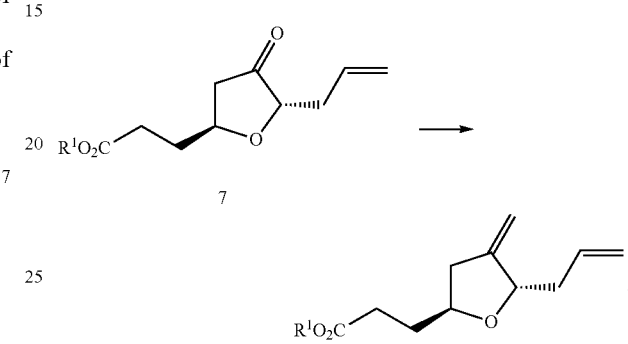

51. The process according to embodiment 50, wherein the step of conversion of the ketone to an alkene is carried out using $Ph_3P=CH_2$, Tebbe's reagent, Petasis reagent, Peterson olefination, Julia olefination, or Kauffman olefination.

52. The process according to embodiment 50 or 51, wherein the compound of formula 7 is formed by the process as defined in any one of embodiments 47 to 49.

53. A process for preparation of a halichondrin analog, comprising the process as defined in any one of embodiments 1-28 and 32-52.

54. A process for preparation of eribulin, comprising the process as defined in any one of embodiments 1-28 and 32-52.

Certain adaptations and modifications of the described embodiments can be made. Therefore, the above discussed embodiments are considered to be illustrative and not restrictive.

What is claimed is:

1. A process for preparation of a compound of formula 11, or a derivative thereof,

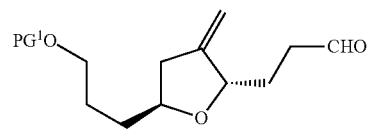

the process comprising:
reducing the compound of formula 8, followed by protecting the resulting alcohol functional group, to form the compound of formula 9, and

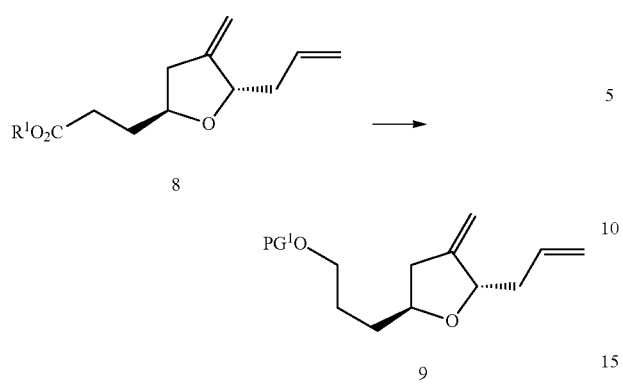

oxidizing the compound of formula 9 to form the compound of formula 11

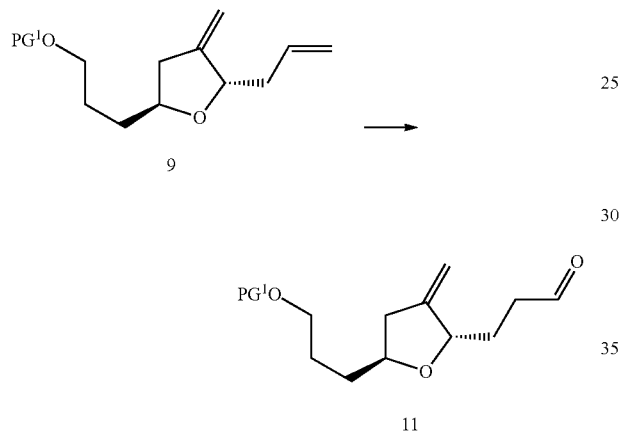

wherein $PG^1$ is an alcohol protecting group, and $R^1$ is H or a hydrocarbon.

2. The process according to claim 1, wherein the step of oxidation of the compound of formula 9 is performed by hydroboration-oxidation to form the compound of formula 10,

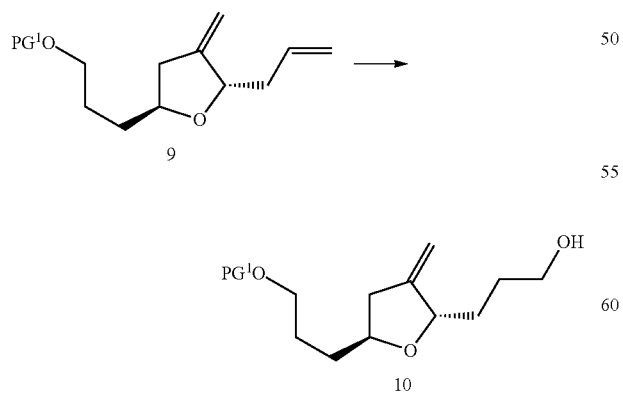

followed by oxidation of the compound of formula 10 to form the compound of formula 11

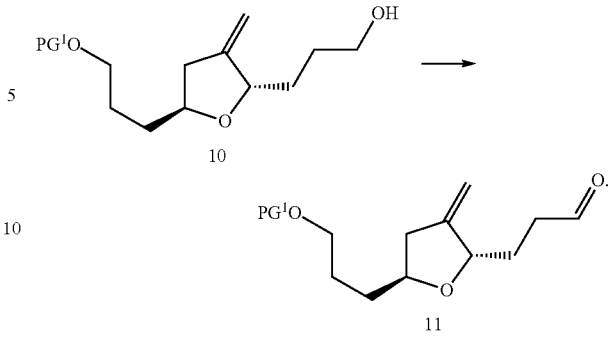

3. The process according to claim 2, wherein the hydroboration oxidation is carried out using disiamylborane (bis-3-methyl-2-butylborane) ($Sia_2BH$), 9-borabycyclo[3,3,1]nonane (9-BBN), dicyclohexylborane ($Chx_2BH$), or dimesitylborane ($(C_6H_2Me_3)_2BH$), along with a peroxide.

4. The process according to claim 2, wherein the step of oxidation of the compound of formula 10 to form the compound of formula 11 is carried out by Collins reagent ($CrO_3.Py_2$), pyridinium dichromate (PDC), Swern oxidation (oxalyl chloride and DMSO), Pfitzner-Moffatt oxidation (carbodiimide and DMSO), Parikh-Doering oxidation (complex $SO_3.Py$ and DMSO), Dess-Martin periodinane, Ley oxidation (catalytic tetrapropylammonium perruthenate (TPAP) in the presence of excess N-methylmorpholine N-oxide (NMO)) or Anelli's oxidation (catalytic 2,2,6,6-Tetramethylpiperidin-1-yl)oxyl (TEMPO) in presence of bleach (NaOCl)).

5. The process according to claim 1, wherein $PG^1$ is acetyl (Ac), benzoyl (Bz), pivaloyl (Piv), benzyl (Bn), β-methoxyethoxymethyl ether (MEM), trityl (Tr), dimethoxy trityl (DMT), methoxymethyl ether (MOM), tert-butyldimethylsilyl (TBDMS), tert-butyldiphenylsilyl (TBDPS), tri-isopropylsilyloxymethyl (TOM), or triisopropylsilyl (TIPS).

6. The process according to claim 1, wherein when $R^1$ is a hydrocarbon, the hydrocarbon is an alkane or aryl, having one or more heteroatoms.

7. The process according to claim 1, wherein the compound of formula 8 is formed by conversion of the ketone functional group in the compound of formula 7 to an alkene functional group, to form the compound of formula 8

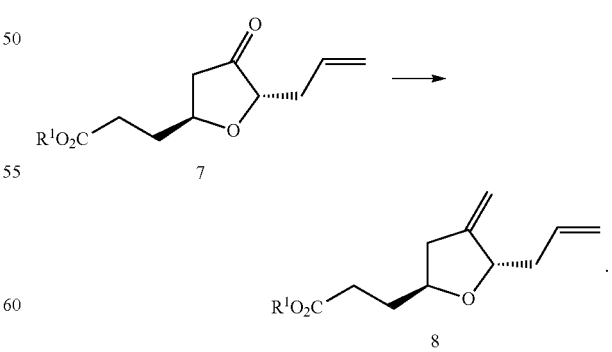

8. The process according to claim 7, wherein the compound of formula 7 is formed by oxidation of the compound of formula 6 to convert the hydroxyl functional group into a ketone functional group

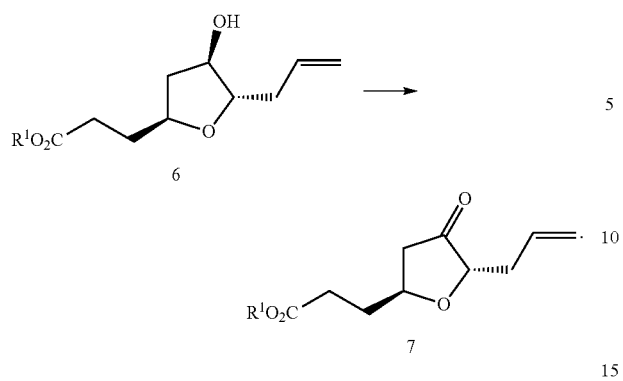
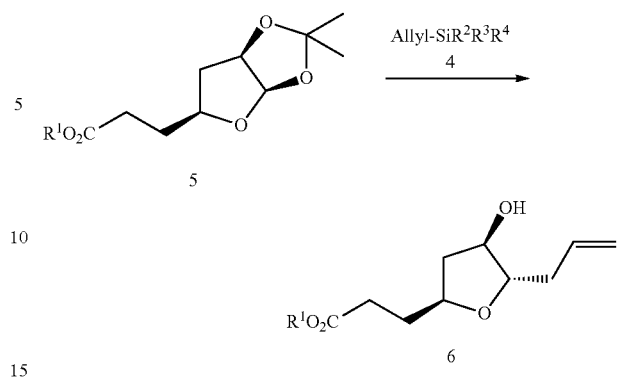
9. The process according to claim 8, wherein the compound of formula 6 is formed by coupling the compound of formula 5 with the allyl-silane of formula 4 to form the compound of formula 6
wherein $R^2$, $R^3$ and $R^4$ each independently is an alkyl, cyclo-alkyl, aryl or hetero-aryl group.
* * * * *